US007060280B2

(12) United States Patent
Lee

(10) Patent No.: US 7,060,280 B2
(45) Date of Patent: Jun. 13, 2006

(54) IMMUNIZATION AGAINST FLAVIVIRUS

(75) Inventor: Sho Tone Lee, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 10/459,155

(22) Filed: Jun. 11, 2003

(65) Prior Publication Data

US 2004/0254365 A1 Dec. 16, 2004

(51) Int. Cl.
*A61K 39/00* (2006.01)
*A61K 39/12* (2006.01)

(52) U.S. Cl. .............................. 424/192.1; 424/186.1; 424/218.1

(58) Field of Classification Search .................. 514/44; 424/218.1, 184.1, 186.1; 530/388.3; 536/23.72
See application file for complete search history.

(56) References Cited

U.S. PATENT DOCUMENTS 6,455,509 B1 * 9/2002 Kochel et al. ................ 514/44
2003/0022849 A1 * 1/2003 Chang ......................... 514/44

FOREIGN PATENT DOCUMENTS

WO WO 200020565 A1 * 4/2000

OTHER PUBLICATIONS

Yasui, K, et al., Analysis of Japanese Encephalitis (JE) Virus Genome and Implications for Recombinant JE Vaccine (1990) Southeast Asian J Trop Med Public Health, vol. 21, No. 4, pp. 663-669.*

Ashok and Rangarajan, Protective efficacy of a plasmid DNA encoding Japanese encephilitis virus envelope protein fused to tissue plasminogen activator signal sequences: studies in a murine intacerebral virus . . . (Feb. 2002) Vaccine vol. 20 pp. 1563-1570.*

Ashok and Rangarajan (2000) Vaccine, vol. 18 pp. 68-75.*

Hsin-Wei Chen et al. "Screening of Protective Antigens of Japanese Encephalitis Virus by DNA Immunization: a Comparative Study with Conventional Viral Vaccines". Journal of Virology, 73(12):10137-10145, Dec. 1999.

Shwn-Chin Chia et al. "Fragment of Japanese encephalitis virus envelope protein produced in *Escherichia coli* protects mice from virus challenge". Microbial Pathogenesis 31:9-19, 2001.

D. Haddad et al. "Characterization of Antibody Responses to a *Plasmodium falciparum* Blood-Stage Antigen Induced by a DNA Prime/Protein Boost Immunization Protocol". Scand. J. Immunol. 49:506-514, 1999.

Eui Konishi et al. "A Highly Attenuated Host Range-Restricted Vaccinia Virus Strain, NYVAC, Encoding the prM, E, and MS1 Genes of Japanese Encephalitis Virus Prevents JEV Viremia in Swine". Virology 190:454-458, 1992.

Eui Konishi et al. "A vipox virus-vectored Japanese encephalitis virus vaccines: use as vaccine candidates in combination with purified subunit immunogens". Vaccine 12(7):633-638, 1994.

Eui Konishi et al. "Comparison of Protective Immunity Elicited by Recombinant Vaccinia Viruses That Synthesize E or NS1 of Japanese Encephalitis Virus". Virology 185:401-410, 1991.

Chien-Hsiung Pan et al. "Protective Mechanisms Induced by a Japanese Encephalitis Virus DNA Vaccine: Requirement for Antibody but Not CD8+ Cytotoxic T-Cell Responses". Journal of Virology 75(23):11457-11463, Dec. 2001.

J. F. L. Richmond et al. "Studies of the Neutralizing Activity and Avidity of Anti-Human Immunodeficiency Virus Type 1 Env Antibody Elicited by DNA Priming and Protein Boosting". Journal of Virology 72(11):9092-9100, Nov. 1998.

Jeong-Im Sin et al: "DNA Priming-Protein Boosting-Enhances Both Antigen-Specific Antibody and Th1-Type Cellular Immune Responses in a Murine Herpes Simplex Virus-2 gD Vaccine Model". DNA and Cell Biology 18(10):771-779, 1999.

Man Ki Song et al. "Enhancement of Immunoglobulin G2a and Cytotoxic T-Lymphocyte Responses by a Booster Immunization with Recombinant Hepatitis C Virus E2 Protein in E2 DNA-Primed Mice". Journal of Virology 74(6):2920-2925, Mar. 2000.

* cited by examiner

*Primary Examiner*—James C. Housel
*Assistant Examiner*—M. Franco Salvoza
(74) *Attorney, Agent, or Firm*—Fish & Richardson P.C.

(57) ABSTRACT

A method of inducing an immune response in a subject against a flavivirus. The method involves administering to the subject with a fusion polypeptide including a signal peptide and a part of an envelope protein of the flavivirus, or with an expression vector containing a nucleic acid encoding the fusion polypeptide. Also disclosed are a polypeptide, an expression vector, and vaccines containing the polypeptide or expression vector.

25 Claims, No Drawings

IMMUNIZATION AGAINST FLAVIVIRUS

BACKGROUND

Flavivirus is a family of arthropod-borne viruses, including dengue virus, yellow fever virus, tick borne encephalitis virus, West Nile encephalitis virus, and Japanese encephalitis virus (JEV). All members of this family can cause diseases in human. In particular, infection of JEV is a leading cause of morbidity and mortality in tropical and sub-tropical regions of Asia. Immunization can be used to protect against JEV. Both inactivated and live-attenuated JEV viruses have been used as vaccines. However, their success has been limited due to lack of long-term immunity and adverse effects such as allergic reactions. Therefore, there is a need for effective and safe vaccines and immunization methods for protection flaviviruses, such as JEV.

SUMMARY

In one aspect, the present invention features a method of inducing an immune response in a subject, such as a human or a non-human animal, against a flavivirus, e.g., JEV, Dengue virus, tick borne encephalitis virus, or West Nile encephalitis virus. The method includes administering to the subject a fusion polypeptide including a signal peptide and a part of an envelope protein (E protein) of the flavivirus, or an expression vector containing a nucleic acid encoding the fusion polypeptide. The signal peptide contains the sequence of VVFTILLLLVAPAYS (SEQ ID NO: 5) and allows the fusion polypeptide to be soluble and correctly folded in a cell. The part of the E protein can be an amino part or a carboxyl part of the E protein. The induced immune response, i.e., the production of antibodies specifically against the flavivirus, can be determined by the assay described in Examples 1–4 or any analogous assays.

To induce an immune response against JEV, a subject can be administered with a first expression vector containing a nucleic acid encoding a fusion polypeptide of the sequence SEQ ID NO: 3, i.e., 1-VVFTILLLLVAPAYSFNCLGMGN-
RDFIEGASGATWVDLVLEGDSCLTIMANDKPTLDVR
MINIEASQLAEVRSYCYHASVTDISTVARCPTTGE AH
NEKRADSSYVCKQGFTDRGWGNGCGLFGKGSIDTC
AKFSCTSKAIGRTIQSENIKYEVGIFVHGTTTSENHG
NYSAQVGASQAAKFTVTPNAPSITLKLGDYGEVT LD
CEPRSGLNTEAFYVMTVGSKSFLVHREFHDLALPWT
PPSSTAWRNRELLMEFEEAHATKQSVVALGSQEGGL
HQALAGAIVVEYSSSVKLTSGHLKCRLKMDK LALK
GTT- 315. This 315-amino acid fusion polypeptide, named $M15E_A$, includes a 15-amino acid fragment (SEQ ID NO: 5, the underlined segment of SEQ ID NO: 3 shown above) of the carboxyl-terminal part of the JEV M protein and a 300-amino acid fragment $E_A$ (SEQ ID NO: 1, the non-underlined segment of SEQ ID NO: 3) of the amino-terminal part of the JEV E protein. One can also administer to a subject a first expression vector containing a nucleic acid encoding another fusion polypeptide $M15E_B$ to induce an immune response. The sequence of $M15E_B$ is shown below:
1-VFTILLLLVAPAYSDKLALKGTTYGMCTEKFSFAK
NPADTGHGTVVIELSYSGSDGPCKIPIVSVA SLNDMT-
PVGRLVTVNPFVATSSANSKVLVEMEPPFGDSYIVV G
RGDKQINHHWYKAGSTLGKAFSTTLKGAQRLAALG
DTAWDFGSIGGVFNSIGKAVHQVFGGAFRT-175 (SEQ ID NO: 11). This fusion polypeptide contains the just-mentioned 15-amino acid fragment (underlined) and a fragment $E_B$ (SEQ ID NO: 2; the non-underlined segment of SEQ ID NO: 11), which contains a 160-amino acid carboxyl-terminal part of the JEV E protein.

In one example, the above-mentioned first expression vector is administered to prime a subject. In general, priming with a vaccine does not induce satisfactory immune response. However, a primed subject can generate strong and long-term immune response after being administered with another vaccine, i.e., boosted. Here, after priming with the first expression vector, the subject can be boosted with the polypeptide $E_A$ (SEQ ID NO: 1, shown above) or $E_B$ (SEQ ID NO: 2shown above). Alternatively, the subject is boosted with a second expression vector containing a nucleic acid encoding $E_A$ or $E_B$. In one embodiment, the subject is primed with a first expression vector containing a nucleic acid encoding $M15E_A$ and boosted with the polypeptide $E_A$. In another embodiment, the subject is primed with a first expression vector containing a nucleic acid encoding $M15E_B$ and boosted with $E_B$.

In another example, a first expression vector encoding $M15E_A$ or $M15E_B$ is administered to boost a subject. Prior to the boosting, the subject is primed with $E_A$ or $E_B$, or a second expression vector containing a nucleic acid encoding $E_A$ or $E_B$. In one embodiment, the subject is primed and boosted respectively with $E_A$ and a first expression vector containing a nucleic acid encoding $M15E_A$.

In yet another example, a subject is primed or boosted with a mixture of a first expression vector and a second expression vector containing nucleic acids encoding $M15rE_A$ and $E_B$ respectively.

Instead of an expression vector encoding $M15E_A$ or $M15E_B$, the $M15E_A$ or $M15E_B$ polypeptide itself can also be administered to a subject to induce an immune response against JEV. The subject can be further administered with $E_A$, $E_B$, or an expression vector containing a nucleic acid encoding $E_A$ or $E_B$.

The present invention also features a method of inducing an immune response in a subject against a JEV by administering the subject with an expression vector containing a nucleic acid encoding $E_B$. Among the expression vector and the polypeptide $E_B$, one of them can be used to prime and the other to boost the subject.

In another aspect, the present invention features an isolated polypeptide having the sequence of SEQ ID NO: 3 (e.g., $M15E_A$) or SEQ ID NO: 11 (e.g., $M15E_B$) and an expression vector containing a nucleic acid encoding such a polypeptide. In the expression vector, a nucleic acid encoding the polypeptide is operably linked to an expression control sequence containing a promoter and, optionally, additional elements such as enhancers. Such an expression vector can be used to transfect cells to thereby produce a polypeptide encoded by the nucleic acid.

In yet another aspect, the present invention features a vaccine for protecting a subject against JEV. The vaccine contains an expression vector having a nucleic acid that encodes a polypeptide of the sequence SEQ ID NO: 2, SEQ ID NO: 3, or SEQ ID NO: 11 and is operably linked to an expression control sequence, and a pharmaceutically acceptable carrier. The present invention also features a vaccine containing a polypeptide of the sequence of SEQ ID NO: 3 or SEQ ID NO: 11, and a pharmaceutically acceptable carrier.

The details of one or more embodiments of the invention are set forth in the accompanying drawings and the description below. Other features, objects, and advantages of the invention will be apparent from the description and drawings, and from the claims.

DETAILED DESCRIPTION

The present invention relates to vaccines and methods to induce an immune response in a subject against a flavivirus, such as JEV.

A flavivirus has a single stranded positive sense RNA genome. For example, the genome of JEV encodes a polyprotein that is proteolytically cleaved into at least 10 proteins in infected cells. These proteins include three structural proteins: an envelope protein (E), a membrane protein (M or precursor M (PrM)), and a capsid protein, and at least seven nonstructural proteins $NS_1$, $NS_{2a}$, $NS_{2b}$, $NS_3$, $NS_{4a}$, $NS_{4b}$, and $NS_5$. The nucleotide sequence corresponding to JEV genorne bp 933–2447 (SEQ ID NO: 21) is shown below.

immunogenic as it is insoluble and does not properly fold when expressed in host cells. $E_B$ is a better immunogen than $E_A$, but still cannot induce a satisfactory immune response in a subject.

The present invention discloses methods using $E_A$ or $E_B$ to induce satisfactory immune response against JEV. The methods are based in part on the unexpected features of a fusion polypeptide $M15E_A$ (SEQ ID NO: 3) encoded by bp 933–1877 of the JEV genome (SEQ ID NO: 8), and another fusion polypeptide $M15E_B$ (SEQ ID NO: 11) encoded by the fusion of bp 933–977 and bp 1851–2330 of the JEV genome (SEQ ID NO: 12). Both fusion polypeptides contain the carboxyl-terminal 15 amino acid fragment of the JEV M protein. This 15 amino acid fragment, encoded by bp

```
GTGGTATTCACCATCCTCCTGCTGTTGGTCGCTCCGGCTTATAGTTTCAACTGTCTGGGA    992
ATGGGCAATCGTGACTTCATAGAAGGAGCCAGTGGAGCCACTTGGGTGGACTTGGTGCTA   1052
GAAGGAGACAGCTGCTTGACAATCATGGCAAACGACAAACCAACATTGGACGTCCGCATG   1112
ATCAACATCGAAGCTAGCCAACTTGCTGAGGTCAGAAGTTACTGCTATCATGCTTCAGTC   1172
ACTGACATCTCGACGGTGGCTCGGTGCCCCACGACTGGAGAAGCCCACAACGAGAAGCGA   1232
GCTGATAGTAGCTATGTGTGCAAACAAGGCTTCACTGATCGTGGGTGGGGCAACGGATGT   1292
GGACTTTTCGGGAAGGGAAGTATTGACACATGTGCAAAATTCTCCTGCACCAGCAAAGCG   1352
ATTGGAAGAACAATCCAGTCAGAAAACATCAAATACGAAGTTGGCATTTTTGTGCATGGA   1412
ACCACCACTTCGGAAAACCATGGGAATTATTCAGCGCAAGTTGGGGCGTCCCAGGCGGCA   1472
AAGTTTACAGTAACACCTAATGCTCCTTCGATAACCCTCAAACTTGGTGACTACGGAGAA   1532
GTCACACTGGACTGTGAGCCAAGGAGTGGACTAAACACTGAAGCGTTTTACGTCATGACC   1592
GTGGGGTCAAAGTCATTTTTGGTCCATAGGGAATGGTTTCATGACCTCGCTCTCCCTTGG   1652
ACGCCCCCTTCGAGCACAGCGTGGAGAAACAGAGAACTCCTCATGGAATTTGAAGAGGCG   1712
CACGCCACAAAACAGTCCGTTGTTGCTCTTGGGTCACAGGAAGGAGGCCTCCATCAGGCG   1772
TTGGCAGGAGCCATCGTGGTGGAGTACTCAAGCTCAGTGAAGTTAACATCAGGCCACCTA   1832
AAATGCAGGCTGAAAATGGACAAACTGGCTCTGAAAGGCACAACCTATGGTATGTGCACA   1892
GAAAAATTCTCGTTCGCGAAAAATCCGGCGGACACTGGTCACGGAACAGTTGTCATTGAA   1952
CTTTCATACTCTGGGAGTGATGGCCCCTGCAAGATTCCGATTGTCTCCGTTGCTAGCCTC   2012
AATGACATGACCCCCGTCGGGCGGCTGGTGACGGTGAACCCCTTCGTCGCGACTTCCAGC   2072
GCCAACTCAAAGGTGCTGGTCGAGATGGAACCCCCCTTCGGAGACTCCTACATCGTAGTT   2132
GGAAGGGGAGACAAGCAGATTAACCACCATTGGTACAAGGCTGGAAGCACGCTGGGCAAA   2192
GCCTTTTCAACGACTTTGAAGGGAGCTCAAAGACTGGCAGCGTTGGGCGACACAGCCTGG   2252
GACTTTGGCTCTATTGGAGGGGTCTTCAACTCCATAGGGAAAGCTGTTCACCAAGTGTTT   2312
GGTGGTGCCTTCAGAACACTCTTTGGGGGAATGTCTTGGATCACACAAGGGCTAATGGGG   2372
GCCCTACTACTTTGGATGGGCATCAACGCACGAGACCGATCAATTGCTTTGGCCTTCTTA   2432
GCCACAGGAGGTGTGCTCGTGTTCTTAGCTACCAATGTGCATGCT                  2477
```

The sequence bp 978–2477 (SEQ ID NO: 9) of the JEV genome encodes the full length E protein (SEQ ID NO: 4). The sequences bp 978–1877 (SEQ ID NO: 6) and bp 1851–2330 (SEQ ID NO: 7) encode $E_A$ and $E_B$, respectively. Attempts have been made to used these two fragments expressed and prepared from *E coli* or mammalian cells to induce immune response in a subject against JEV. $E_A$ is not 933–977 (SEQ ID NO: 10) of the JEV genome functions as a signal peptide, rendering the fusion polypeptides soluble. Also, as the fusion polypeptides can properly fold in host cells, they can be prepared by recombinant methods.

To prepare a fusion polypeptide described above, a nucleic acid encoding the polypeptide, e.g., SEQ ID NO: 8 or SEQ ID NO: 12, can be ligated into a recombinant expression vector, where the nucleic acid is operatively linked to a regulatory sequence suitable for a host cell for expressing the polypeptide. Examples of such a regulatory sequence include promoters, enhancers and other expression control elements that are known to those skilled in the art. Such an expression vector can be used to transfect host cells to thereby produce a protein or polypeptide of the invention. The recombinant expression vector of the invention can be designed for expression of polypeptides in prokaryotic or eukaryotic cells. For example, polypeptides can be expressed in bacterial cells such as *E. coli*, insect cells (using baculovirus), yeast cells, mammalian cells, or other suitable host cells. See Goeddel, (1990) *Gene Expression Technology: Methods in Enzymology* 185, Academic Press, San Diego, Calif. The expressed fusion polypeptide can be purified from corresponding host cells by methods well known in the art, including ammonium sulfate precipitation and fractionation column chromatography (e.g., ion exchange, gel filtration, electrophoresis, affinity chromatography, etc.). The purified polypeptide can then be used in a vaccine to induce immune response in a subject against JEV in the manner described in Examples 1–4 below. The above-described expression vector can also be used to induce immune response in a subject against JEV.

The vaccine of this invention can contain pharmaceutically suitable carriers, diluents or excipient, such as sterile water, physiological saline, or the like. The vaccine can also contain adjuvant materials, such Freund's Complete Adjuvant (FCA) or Freund's Incomplete Adjuvant (ICA) to enhance an immune response.

To achieve a satisfactory immune response, the above-mentioned expression vectors or polypeptides are introduced into the subject at different times and, optionally, via different routes. Both of the expression vectors and the polypeptides can be used to prime or boost the immune response as described in Examples 2 and 3 below. The expression vectors can be introduced into the subject via intramuscular injection or the gene gun as described in Chen H W et al., J. Virol. 73: 10137–10145, 1999. The fusion polypeptide can be introduced into the subject in the manner described in Example 2 below. After introducing the expression vectors or polypeptides, the immune response in the subject can be evaluated following the procedures described in Example 4 below.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

1. Animals. Female $C_3H$/HeN mice (6–7 weeks old) were purchased from the National Laboratory Animal Breeding and Research Center (Taipei, Taiwan). The care of the animals was provided in accordance with guidelines approved by the animal committee of the Institute of Biomedical Sciences, Academia Sinica.

2. Virus. The JEV strain Beijing-1 was maintained in suckling mouse brain and prepared as described in Chia S C et al., Microbial. Patho. 31: 9–19, 2001. To determine the 50% lethal dose ($LD_{50}$), groups of mice (10–12 weeks old) were infected with a 10-fold serial dilution of JEV Beijing-1 followed by an intracerebral inoculation of 30 μl of phosphate buffered saline (PBS) (sham inoculation) to increase the susceptibility of infection of the central nervous system. A formalin-inactivated mouse-brain-derived JEV reference vaccine (Beijing strain, Tanabe Seiyaku Co., Osaka, Japan) was used as a positive control antigen. The $LD_{50}$ dose for $C_3H$/HeN mice was found to be $1\times10^4$ pfu/mouse.

3. Plasmids for DNA immunizations. Fragments of the gene encoding the E protein of JEV Beijing-1 were prepared from the plasmid p15ME (Chen H W et al., J. Virol. 73: 10137–10145, 1999) by PCR. This plasmid contains a cDNA segment encoding the full-length E protein and the carboxyl-terminal 15 amino acid of the membrane protein. This cDNA segment corresponds to nucleotide bases 933–2477 of the JEV genome and was constructed into the pcDNA3 vector (Invitrogen, San Diego). The double-stranded subfragments of JEV E gene were obtained by PCR using appropriate primer sets shown below:

```
M15EA upstream:     5'-CGCGGATCCAAATGGTGGTATTCACCATC-3'  (SEQ ID NO: 13)
M15EA downstream:   5'-TTTTCTAGAGCTTAGGTTGTGCCTTTCAG-3'  (SEQ ID NO: 14)
EA upstream:        5'-CGCGGATCCAAATGTTCAACTGTCTGGGA-3'  (SEQ ID NO: 15)
EA downstream:      5'-TTTTCTAGAGCTTAGGTTGTGCCTTTCAG-3'  (SEQ ID NO: 16)
M15EB upstream:     5'-CGCGGATCCAAATGGTGGTATTCACCATC-3'  (SEQ ID NO: 17)
M15EB downstream:   5'-TTTTCTAGACGTTATGTTCTGAAGGCACC-3'  (SEQ ID NO: 18)
EB upstream:        5'-GCTGCATATGGACAAACTGGCTCTG-3'      (SEQ ID NO: 19)
EB downstream:      5'-TTTTCTAGACGTTATGTTCTGAAGGCACC-3'  (SEQ ID NO: 20)
```

The upstream primers contain a BamHI site and an ATG start codon, and the downstream primer contains a stop codon and an EcoRI site to facilitate cloning. The PCR products were ligated into a PCR-Blunt vector (Invitrogen, San Diego) for enzyme mapping and sequencing. The identified plasmids were then digested with appropriate restriction enzymes to release DNA fragments containing bp 933–1877, 978–1877, and 1851–2330 of the JEV genome. The first fragment encodes a 15 amino acid signal peptide preceding the E protein and the amino-terminal part of the E protein ($E_A$). The latter two fragments encode $E_A$ and $E_B$ protein fragments and make up 90% of the E protein, excluding the transmembrane domain and cytoplasmic tail (49 amino acids). These fragments were inserted into the pcDNA3 vector to produce pM15$E_A$, pM15$E_B$, p$E_A$, and p$E_B$, respectively. M15 indicates the nucleic acid 933 to 978 encoding the 15-amino acid signal peptide. These eukaryotic expression vectors contain the cytomegalovirus early promoter-enhancer sequence and the polyadenylation and the 3'-splicing signals from bovine growth hormone. Plasmid DNA was purified from transformed *Escherichia coli* DH5α by Qiagen Plasmid Giga Kits in accordance with the manufacturer's instructions and stored at −70° C. as pellets. The DNA was reconstituted in sterile saline at a concentration of 1 mg/ml before use.

4. Cloning and expression of JEV E protein fragment in *E. coli*. The cloning and expressing of $E_A$ and $E_B$ in *E. coli* were conducted in the same manner as described in Chia S C et al., Microbial. Patho. 31: 9–19, 2001. Briefly, the PCR products containing DNA encoding $E_A$ (bp 978–1877) and $E_B$ (bp 1851–2330) were inserted into the pET-28A vector (Novagen, Madison, Wis.) to obtain pET-$E_A$ and pET-$E_B$. These vectors were transformed into *E. coli* JM109/$DE_3$ respectively. The expressions of the proteins in the transformed *E. coli* were induced by culturing the *E. coli* in the presence of isopropyl thio-β-D-galactopyranoside (IPTG) for 6 hours at 30° C. The expressed proteins were purified by Nickel columns, and their amino acid sequences confirmed by the MALDI-TOF (Matrix assisted laser desorption—time of flight, Applied Biosystems, Foster City, Calif.) analysis. The recombinant proteins thus prepared were named as r$E_A$ and r$E_B$ to differentiate from plasmids p$E_A$ and p$E_B$.

5. Immunization. The above-mentioned female $C_3H$/HeN mice were immunized intramuscularly (im) with the purified proteins r$E_A$ or r$E_B$ according to the method described in Chia S C et al., Microbial. Patho. 31: 9–19, 2001. The mice were divided into 6 groups. Mice in Groups 1–3 were injected into each quadriceps muscle with r$E_A$ at a dose of 25 μg/injection for once, twice, and three times, respectively. Mice in Groups 4–6 were injected r$E_B$ in a similar manner. For the first injections and the following injections, the polypeptides were mixed with CFA and IFA, respectively.

Two weeks after the last injection, the immunized mice were challenged with lethal doses of JEV according to the method described in Chia S C et al., Microbial. Patho. 31: 9–19, 2001. Briefly, each of the mice was challenged intraperitonealy (ip) with JEV Beijing-I at a dose of 50 times of the $LD_{50}$. The JEV-challenged mice were observed daily for symptoms of viral encephalitis as described in McMinn P J. of general virol. 78:2711–2722, 1991 for 30 days. The percentage of mice that survived in each group (i.e., the survival rate or level of protection) was determined.

The results indicated that the injection of r$E_B$ for once, twice, and three times led to 20%, 27%, 58% levels of protection, respectively. The injection of r$E_A$, on the other hand, showed no protection even after three injections. These results were comparable to those described in Chia S C et al., Microbial. Patho. 31: 9–19, 2001, suggesting that r$E_A$, an insoluble protein, is less antigenic and less immunogenic, while r$E_B$, a soluble protein, is antigenic and immunogenic.

Female $C_3H$/HeN mice were also immunized im with the plasmids: pcDNA3, pM15$E_A$, p$E_A$, or p$E_B$ One week before the immunization, each mouse was injected with 200 μl of 10 μM cardiotoxin (Sigma, St. Louis) in the quadricep muscles on two of its legs (100 ul each). These mice were divided into 12 groups (Groups 1–12), anesthetized, and given different immunization regimens as indicated below in Table 1, column 2. The mice in Groups 1 and 2 were injected once with a control vaccine (Tanabe Seiyaku Co., Osaka, Japan) and saline at a dose of 100 ul/injection, respectively. The mice in Groups 3, 4, and 9 were injected once, respectively, with $pcDNA_3$, p$E_A$, and p$E_B$ at a dose of 50 μg/injection. The mice in Groups 5–8 and 10–11 were injected, respectively, with pcDNA3, pM15$E_A$, p$E_A$, and p$E_B$ at a dose of 50 μg/injection for twice or three times at 2 week-intervals. The mice in Group 12 were injected with a mixture of p15M$E_A$ and p$E_B$ at a dose of 50 μg/injection for three times at 2 week-intervals.

Two weeks after the last injection, the mice in each group were challenged with lethal doses of JEV and the survival rates determined in the same manner described above. The results were summarized in Table 1.

TABLE 1

Effects of Immunization by vectors containing JEV envelope (E) gene

| Group No. | Immunization regimens (number of injection(s)) | Number of mice surviving after a JEV challenge/ Number of mice challenged | Survival rate (%) |
|---|---|---|---|
| 1 | Control Vaccine | 24/24 | 100.00** |
| 2 | Saline | 4/20 | 20.00 |
| 3 | $PcDNA_3$ | 5/25 | 20.00 |
| 4 | p$E_A$ (1) | 2/10 | 20.00 |
| 5 | p$E_A$ (2) | 3/11 | 27.27 |
| 6 | p$E_A$ (3) | 5/25 | 20.00 |
| 7 | pM15$E_A$ (2) | 3/10 | 30.00 |
| 8 | pM15$E_A$ (3) | 13/24 | 54.17* |
| 9 | p$E_B$ (1) | 2/10 | 20.00 |
| 10 | p$E_B$ (2) | 2/9 | 22.22 |
| 11 | p$E_B$ (3) | 12/30 | 40.00* |
| 12 | pM15$E_A$ + p$E_B$ (3) | 14/19 | 73.68** |

*$p < 0.01$,
**$p < 0.001$ by Fisher's exact test compared to value for Group 2.

As shown in Table 1, the injections of p$E_A$ for once, twice, and three times (Groups 4, 5, and 6) led to 20%, 27.27% and 30% levels of protection, which are not significantly different from that by the injection of pcDNA3. In contrast, the injection of pM15$E_A$ (3 times) led to a 54% level of protection (Group 8), which is significantly greater than that by the injection of pcDNA3. Since pM15$E_A$ encodes a polypeptide containing a 15-amino acid signal peptide (rM15$E_A$) while p$E_A$ encodes a polypeptide without the signal peptide, these results suggest the importance of this signal peptide for rM15$E_A$ to be immunogenic.

Also as shown in Table 1, the injection of p$E_B$ protected mice from the lethal JEV challenge only after three injections (Group 11). Interestingly, after being immunized with pM15$E_A$ and p$E_B$, most (73.6%) of the mice in Group 12 were protected against the lethal virus challenge.

EXAMPLE 2

Mice were immunized by a DNA priming-protein boosting immunization protocol, and challenged with lethal doses of JEV.

Mice were pretreated with cardiotoxin in the same manner described above in Example 1. One week later, the mice were divided into 10 groups. The mice in Groups 1, 2, and 3 were injected with a control vaccine, pcDNAs, and saline, respectively in the same manner described above in Example 1. The mice in Groups 4 and 7 were respectively primed with pM15$E_A$ and p$E_B$ twice at a dose of 50 μg/injection. The mice in Groups 5 and 6 were primed with pM15$E_A$ (50 μg/injection) twice, and two weeks later, boosted with r$E_A$ (25 μg/injection) once and twice, respectively. The mice in Groups 8 and 9 were primed with p$E_B$ (50

μg/injection) twice, and boosted with $rE_B$ (25 μg/injection) once and twice, respectively. Finally, the mice in Group 10 were primed with $pM15E_B$ twice (50 μg/injection) and boosted with $rE_B$ twice (25 μg/injection).

Two weeks after the last injection, the mice in each group were challenged with lethal doses of JEV and the survival rates determined in the same manner described above in Example 1. The results were summarized in Table 2.

TABLE 2

Effects of Immunization by DNA priming - protein boosting

| Group No. | Immunization regimens (number of injection(s)) | Number of mice surviving after a virus challenge/Number of mice challenged | Survival rate (%) |
|---|---|---|---|
| 1 | Vaccine | 10/10 | 100.00** |
| 2 | $pcDNA_3$ | 4/13 | 30.70 |
| 3 | Saline | 2/8 | 25.00 |
| 4 | $pM15E_A$ (2) | 3/12 | 30.00 |
| 5 | $pM15E_A$ (2) + $rE_A$ (1) | 5/10 | 50.00* |
| 6 | $pM15E_A$ (2) + $rE_A$ (2) | 9/10 | 90.00** |
| 7 | $pE_B$ (2) | 2/9 | 22.20 |
| 8 | $pE_B$ (2) + $rE_B$ (1) | 4/10 | 40.00* |
| 9 | $pE_B$ (2) + $rE_B$ (2) | 13/18 | 72.20** |
| 10 | $pM15E_B$ (2) + $rE_B$ (2) | 18/18 | 100.00** |

*$p < 0.01$,
**$p < 0.001$ by Fisher's exact test compared to value of Group 2.

As shown in Table 2, the injections (twice) of $pM15E_A$ or $pE_B$ alone provided no protection against the JEV challenge. Unexpectedly, priming with $pM15E_A$ twice followed by one or two boostings with non-immunogenic $rE_A$ (Groups 5 and 6) led to levels of protection (50% and 90%) significant higher than that by pcDNA3 or saline. The level of protection in Group 6 was almost equal to that the control vaccine. These results indicate that, if the priming is sufficient, the non-immunogenic $rE_A$ can serve as an effective immunogen.

Priming with $pE_B$ twice followed by one or two boostings with $rE_B$ (Groups 8 and 9) led to significant levels of protection (40% and 72.2%). These levels of protection are much higher than those resulted from injection of $pE_B$ (twice) or $rE_B$ (twice, see Table 1) alone, indicating DNA priming-protein boosting regimen is more effective DNA only or protein only regimen. Finally, it is unexpected that all mice were protected against from JEV if they had been primed twice with $pM15E_B$ and boosted twice with $rE_B$ (Group 10). These results suggest that the M15 signal peptide could increase the immunogenicity of $E_B$.

EXAMPLE 3

Mice were immunized by a protein priming-DNA boosting immunization protocol, and challenged with lethal doses of JEV.

Mice were divided into 6 groups. Those in Groups 1, 2, and 3 were injected once with a control vaccine, pcDNAs, and saline, respectively, in the same manner described above in Example 1. The mice in Groups 4, 5, and 6 were primed by intramuscular injection of 25 μg $rE_A$ or $rE_B$ protein (prepared in CFA), and, two weeks later, were primed again by 25 μg $rE_A$ or $rE_B$ protein prepared in IFA. One week later, the mice in these three groups were treated with 100 μl of 10 μM cardiotoxin in each quadricep muscle. One and three weeks later, the mice in these three groups were, respectively, boosted with $pM15E_A$, $pE_A$, and $pE_B$ at a dose of 25 μg/boosting. The mice in each group were challenged with lethal doses of JEV and the survival rates determined in the same manner described above in Example 1. Two independent experiments were performed for each group. The results were summarized in Table 3.

TABLE 3

Effects of Immunization by Protein priming - DNA boosting.

| Group No. | Immunization regimens (number of injection(s)) | Number of mice surviving after a virus challenge/ Number of mice challenged | Survival rate (%) |
|---|---|---|---|
| 1 | Vaccine | 9/10 | 90.00** |
| 2 | Saline | 2/10 | 20.00 |
| 3 | $PcDNA_3$ | 2/10 | 20.00 |
| 4 | $rE_A$ (2) + $pM15E_A$ (2) | 8/8 | 100.00** |
| 5 | $rE_A$ (2) + $pE_A$ (2) | 1/8 | 12.50 |
| 6 | $rE_B$ (2) + $pE_B$ (2) | 5/7 | 71.43** |

*$p < 0.01$,
**$p < 0.001$ by Fisher's exact test compared to value of Group 2.

As shown in Table 3, 100% and 71.43% of the mice in Groups 4 and 5 were protected from the lethal JEV challenges. These levels of protection were highly significant and comparable to those in the groups of mice that were DNA-primed and protein-boosted as described above in Example 1 above (see Table 2, Groups 6 and 9). In contrast, only 12.5% of the mice in Group 5 were protected, indicating the importance of the 15-amino acid signal peptide in the immunogenic activity of $M15E_A$.

Examples 2 and 3 described above have indicated unexpected results: $rE_A$ by itself is non-immunogenic or non-protective, but it acts as an excellent immunogen in either priming or boosting. One reason for these results is that $rE_A$ contains certain minor epitopes. Although $rE_A$ is not immunogenic by itself, it can induce a full-fledge secondary immune response if a priming or the boosting agent is immunogenic (e. g., $pM_{15}E_A$).

EXAMPLE 4

Survived mice from the groups described above in Examples 1–3 were tested for the presence anti-JEV E protein antibodies according to the ELISA method described in Chia et al., Microbial. Patho. 31: 9–19, 2001.

It is known that different immunization approaches (e.g., different antigen delivery routes) can affect the antibody isotypes and T helper cell types in an immune response. For example, intramuscular injection of DNA generates almost exclusively IgG2a antibody due to $Th_1$-cell activation. In contrast, gene gun delivery of plasmid DNA mostly leads IgG1 antibody production, which is enhanced by $Th_2$-cell activation. Further, $Th_2$-cell activation suppresses IgG2a production.

To test the presence of anti-JEV E protein antibodies, serum samples were collected from 4–5 mice in each group subjected to above-mentioned immunization regimens at 2 days before (prechallenge) and 2 weeks after (postchallenge) the virus challenges. Each sample was added to a well on a microtiter plate that was coated with JEV prepared from tissue culture. Anti-JEV E protein antibodies in the sample would bind to the JEV.

To detect IgG in the sample, the plate was then incubated with an HRP-conjugated goat anti-mouse IgG Fc (1:1000, ICN/Cappel, Aurora, Ohio). After color was developed by incubating with ABTS, the absorbance at 405 nm was measured on an ELISA reader. The resultant reading indicated the level of IgG in the sample.

To detect IgG1 or IgG2a isotype in the sample, the plate were incubated with biotin-conjugated rat anti-mouse IgG1

(1:1000; PharMingen, San Diego, Calif.) or rat anti-mouse IgG2a (1:1000; PharMingen). The results were visualized by Avidin-HRP (1:2000; PharMingen) and ABTS, and the absorbance at 405 nm measured in the same manner as described above.

The results indicated that, in general, the $OD_{405}$ readings of IgG2a were greater than those of IgG1 irrespective of the immunization regimens. At the prechallenge stage, the IgG2a and IgG1 OD405 levels did not vary very much from group to group except in the samples from mice subjected to the DNA priming—protein boosting or protein priming—DNA boosting regimen. In such mice, the IgG2a levels were significantly higher than those of IgG1. At the postchallenge stage, the IgG2a level in each group increased significantly, while the IgG1 level only increased slightly. Also, the level of IgG2a was much greater than those of IgG1 (p ranging from <0.01 to <0.001). Further, $E_A$ antigen tended to lead to higher IgG2a level than any other antigens, while $pcDNA_3$ led to low levels of both IgG1 and IgG2a.

To examine the ability of antisera collected from immunized mice to neutralize JEV virus, a plaque reduction neutralization test (PRNT) was conducted in the same manner as the "50% plaque reduction assay with BHK-21 cells" described in Johnson M P et al., p. 189–192. In H. Ginsberg, F. Brown, R. A. Lerner, and R. M. Chanock (ed.), Vaccines 88. Cold Spring Harbor Laboratory, Cold Spring Harbor, N.Y.

Serum samples were collected from the mice in the groups described above in Example 1–3 at 2 days before (prechallenge) and 2 weeks after (postchallenge) the virus challenges. The samples were serially diluted in 5% BCS-PBS and incubated at 56° C. for 30 minutes to inactivate complement. Each sample was then mixed with an equal volume of minimum essential medium (MEM)-BCS containing JEV to yield a mixture containing approximately 1000 pfu of virus/ml. The mixture was incubated at 4° C. for 18–21 hours and then added to a well in a six-well plate (in triplicates) containing confluent monolayers of BHK-21 cells. The plate was then incubated at 37° C. for 1 hour and gently rocked every 15 minutes. The wells of the plate were then overlaid with 2 ml of 1% methyl cellulose prepared in MEM supplemented with 5% BCS and incubated at 37° C. in 5% $CO_2$ for 4 days.

After plaques appeared in the wells, they were stained with naphthol blue black and counted under a microscope. The neutralization antibody titer was calculated as the reciprocal of the highest dilution resulting in 50% reduction of plaques as compared to that of a control JEV virus in the absence of any antiserum. At least three serum samples from each group were determined for the PRNT titer. Results were shown in Table 4.

TABLE 4

Effects of immunizations on neutralizing antibody titres and on survival rates

| Groups | Immunization regimens | Plaque neutralization titers Prechallenge | Postchallenge | Survival rate (%) |
|---|---|---|---|---|
| 1 | Vaccine | 1:80 | >1:1280 | 100% |
| 2 | Saline | <1:5 | 1:40 | 20% |
| 3 | $pcDNA_3$ | 1:5 | 1:40 | 20% |
| 4 | $pM_{15}E_A$ | 1:5 | 1:160 | 54% |
| 5 | $pE_A$ | <1:5 | 1:40 | 20% |
| 6 | $pE_B$ | 1:5 | 1:40 | 40% |
| 7 | $pM_{15}E_A + pE_B$ | 1:5 | 1:640 | 74% |
| 8 | $pM_{15}E_A + rE_A$ | 1:40 | 1:640 | 90% |
| 9 | $pE_B + rE_B$ | 1:10 | 1:640 | 72% |
| 10 | $rE_A + pE_A$ | <1:5 | 1:40 | 13% |
| 11 | $rE_A + pM_{15}E_A$ | 1:20 | 1:640 | 100% |
| 12 | $rE_B + pE_B$ | 1:5 | 1:320 | 71% |

Numbers underlined: only one determination was done due to limited amount of serum available.

As shown in Table 4, at the prechallenge stage, the mice in most of the groups had low PRNT titers raging from 1:5 to 1:10, except those had been immunized with a control vaccine (Group 1), $pM15E_A$ +$rE_A$ (Group 8), and $rE_A$ +$pM15E_A$ (Group 11). The mice in these 3 groups had PRNT titers ranging from 1:20 to 1:80. At the postchallenge stage, the PRNT titers of mice in all groups increased considerably and correlated positively with the survival rate of mice in respective groups. In general, it appeared that a PRNT titer of 1:40 was enough to protect against the virus infection.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of inducing an immune response in a subject against a flavivirus, the method comprising administering to the subject a fusion polypeptide including a signal peptide and a part of an envelope protein of the flavivirus, or an expression vector containing a nucleic acid encoding the fusion polypeptide, wherein the signal peptide contains SEQ ID NO: 5 and SEQ ID NO: 5 is located at the amino terminus of the fusion polypeptide.

2. The method of claim 1, wherein the flavivirus is a Japanese encephalitis virus.

3. The method of claim 2, wherein the part of the envelope protein is an amino terminal part or a carboxyl terminal part of the envelope protein.

4. The method of claim 4, wherein the subject is administered a first expression vector containing a nucleic acid encoding a fusion polypeptide of the sequence SEQ ID NO: 3 or 11.

5. The method of claim 5, wherein the first expression vector is administered to prime the subject.

6. The method of claim 5, wherein, after performing the administering step, the subject is boosted by administering a polypeptide of the sequence SEQ ID NO: 1 or SEQ ID NO: 2, or a second expression vector containing a nucleic acid encoding a polypeptide of the sequence SEQ ID NO: 1 or SEQ ID NO: 2.

7. The method of claim 6, wherein the subject is primed with the first expression vector containing the nucleic acid encoding the fusion polypeptide of the sequence of SEQ ID NO: 3 and boosted with the polypeptide of the sequence SEQ ID NO: 1.

8. The method of claim 6, wherein the subject is primed with the first expression vector containing the nucleic acid encoding the fusion polypeptide of the sequence of SEQ ID NO: 11 and boosted with the polypeptide of the sequence SEQ ID NO: 2.

9. The method of claim 4, wherein first expression vector is administered to boost the subject.

10. The method of claim 9, wherein, before performing the administering step, the subject is primed by administering a polypeptide of the sequence SEQ ID NO: 1 or SEQ ID NO: 2 or a second expression vector containing a nucleic acid encoding a polypeptide of the sequence SEQ ID NO: 1 or SEQ ID NO: 2.

11. The method of claim 10, wherein the subject is primed with the polypeptide of the sequence SEQ ID NO: 1 and is boosted with the first expression vector containing the nucleic acid encoding the fusion polypeptide of the sequence of SEQ ID NO: 3.

12. The method of claim 4, wherein the subject is further administered a second expression vector containing a nucleic acid encoding a polypeptide of the sequence SEQ ID NO: 2.

13. The method of claim 3, wherein the subject is administered a fusion polypeptide of the sequence SEQ ID NO: 3 or 11.

14. The method of claim 13, wherein the subject is further administered a polypeptide of the sequence SEQ ID NO: 1 or an expression vector containing a nucleic acid encoding a polypeptide of the sequence SEQ ID NO: 1.

15. The method of claim 13, wherein the subject is further administered a polypeptide of the sequence SEQ ID NO: 2 or an expression vector containing a nucleic acid encoding a polypeptide of the sequence SEQ ID NO: 2.

16. The method of claim 1, wherein the flavivirus is a Dengue virus, a tick borne encephalitis virus, or a West Nile encephalitis virus.

17. The method of claim 1, wherein the part of the envelope protein is an amino terminal part or a carboxyl terminal part of the envelope protein.

18. A method of inducing an immune response in a subject against a Japanese encephalitis virus, the method comprising administering to the subject an expression vector containing a nucleic acid encoding a polypeptide of the sequence SEQ ID NO: 2.

19. The method of claim 18, wherein the expression vector and a polypeptide having the seguence as set forth in SEQ ID NO: 2 are administered to prime and boost the subject, respectively.

20. The method of claim 18, wherein a polypeptide having the sequence as set forth in SEQ ID NO: 2 and the expression vector are administered to prime and boost the subject, respectively.

21. An isolated polypeptide comprising the sequence SEQ ID NO: 3 or 11.

22. An expression vector comprising a nucleic acid encoding a polypeptide of the sequence SEQ ID NO: 3 or 11, wherein the nucleic acid is operably linked to an expression control sequence.

23. An immunogenic agent comprising an expression vector containing a nucleic acid that encodes a polypeptide of the sequence SEQ ID NO: 2, 3, or 11 and is operably linked to an expression control sequence, and a pharmaceutically acceptable carrier.

24. An immunogenic agent comprising a polypeptide of the sequence of SEQ ID NO: 3 or 11, and a pharmaceutically acceptable carrier.

25. An immunogenic agent comprising a nucleic acid that encodes a polypeptide of SEQ ID NO: 2 or 3, and a pharmaceutically acceptable carrier.

* * * * *

SEQUENCE LISTING

```
<160> NUMBER OF SEQ ID NOS: 21

<210> SEQ ID NO 1
<211> LENGTH: 300
<212> TYPE: PRT
<213> ORGANISM: Japanese encephalitis virus

<400> SEQUENCE: 1

Phe Asn Cys Leu Gly Met Gly Asn Arg Asp Phe Ile Glu Gly Ala Ser
 1               5                  10                  15
```

-continued

```
Gly Ala Thr Trp Val Asp Leu Val Leu Glu Gly Asp Ser Cys Leu Thr
            20                  25                  30

Ile Met Ala Asn Asp Lys Pro Thr Leu Asp Val Arg Met Ile Asn Ile
        35                  40                  45

Glu Ala Ser Gln Leu Ala Glu Val Arg Ser Tyr Cys Tyr His Ala Ser
    50                  55                  60

Val Thr Asp Ile Ser Thr Val Ala Arg Cys Pro Thr Thr Gly Glu Ala
65                  70                  75                  80

His Asn Glu Lys Arg Ala Asp Ser Ser Tyr Val Cys Lys Gln Gly Phe
                85                  90                  95

Thr Asp Arg Gly Trp Gly Asn Gly Cys Gly Leu Phe Gly Lys Gly Ser
            100                 105                 110

Ile Asp Thr Cys Ala Lys Phe Ser Cys Thr Ser Lys Ala Ile Gly Arg
        115                 120                 125

Thr Ile Gln Ser Glu Asn Ile Lys Tyr Glu Val Gly Ile Phe Val His
    130                 135                 140

Gly Thr Thr Thr Ser Glu Asn His Gly Asn Tyr Ser Ala Gln Val Gly
145                 150                 155                 160

Ala Ser Gln Ala Ala Lys Phe Thr Val Thr Pro Asn Ala Pro Ser Ile
                165                 170                 175

Thr Leu Lys Leu Gly Asp Tyr Gly Glu Val Thr Leu Asp Cys Glu Pro
            180                 185                 190

Arg Ser Gly Leu Asn Thr Glu Ala Phe Tyr Val Met Thr Val Gly Ser
        195                 200                 205

Lys Ser Phe Leu Val His Arg Glu Trp Phe His Asp Leu Ala Leu Pro
    210                 215                 220

Trp Thr Pro Pro Ser Ser Thr Ala Trp Arg Asn Arg Glu Leu Leu Met
225                 230                 235                 240

Glu Phe Glu Glu Ala His Ala Thr Lys Gln Ser Val Val Ala Leu Gly
                245                 250                 255

Ser Gln Glu Gly Gly Leu His Gln Ala Leu Ala Gly Ala Ile Val Val
            260                 265                 270

Glu Tyr Ser Ser Ser Val Lys Leu Thr Ser Gly His Leu Lys Cys Arg
        275                 280                 285

Leu Lys Met Asp Lys Leu Ala Leu Lys Gly Thr Thr
    290                 295                 300


<210> SEQ ID NO 2
<211> LENGTH: 160
<212> TYPE: PRT
<213> ORGANISM: Japanese encephalitis virus

<400> SEQUENCE: 2

Asp Lys Leu Ala Leu Lys Gly Thr Thr Tyr Gly Met Cys Thr Glu Lys
 1               5                  10                  15

Phe Ser Phe Ala Lys Asn Pro Ala Asp Thr Gly His Gly Thr Val Val
            20                  25                  30

Ile Glu Leu Ser Tyr Ser Gly Ser Asp Gly Pro Cys Lys Ile Pro Ile
        35                  40                  45

Val Ser Val Ala Ser Leu Asn Asp Met Thr Pro Val Gly Arg Leu Val
    50                  55                  60

Thr Val Asn Pro Phe Val Ala Thr Ser Ser Ala Asn Ser Lys Val Leu
65                  70                  75                  80

Val Glu Met Glu Pro Pro Phe Gly Asp Ser Tyr Ile Val Val Gly Arg
                85                  90                  95
```

-continued

Gly Asp Lys Gln Ile Asn His His Trp Tyr Lys Ala Gly Ser Thr Leu
100 105 110

Gly Lys Ala Phe Ser Thr Thr Leu Lys Gly Ala Gln Arg Leu Ala Ala
115 120 125

Leu Gly Asp Thr Ala Trp Asp Phe Gly Ser Ile Gly Gly Val Phe Asn
130 135 140

Ser Ile Gly Lys Ala Val His Gln Val Phe Gly Gly Ala Phe Arg Thr
145 150 155 160

<210> SEQ ID NO 3
<211> LENGTH: 315
<212> TYPE: PRT
<213> ORGANISM: Artificial Sequence
<220> FEATURE:
<223> OTHER INFORMATION: Synthetically generated peptide

<400> SEQUENCE: 3

Val Val Phe Thr Ile Leu Leu Leu Leu Val Ala Pro Ala Tyr Ser Phe
1 5 10 15

Asn Cys Leu Gly Met Gly Asn Arg Asp Phe Ile Glu Gly Ala Ser Gly
20 25 30

Ala Thr Trp Val Asp Leu Val Leu Glu Gly Asp Ser Cys Leu Thr Ile
35 40 45

Met Ala Asn Asp Lys Pro Thr Leu Asp Val Arg Met Ile Asn Ile Glu
50 55 60

Ala Ser Gln Leu Ala Glu Val Arg Ser Tyr Cys Tyr His Ala Ser Val
65 70 75 80

Thr Asp Ile Ser Thr Val Ala Arg Cys Pro Thr Thr Gly Glu Ala His
85 90 95

Asn Glu Lys Arg Ala Asp Ser Ser Tyr Val Cys Lys Gln Gly Phe Thr
100 105 110

Asp Arg Gly Trp Gly Asn Gly Cys Gly Leu Phe Gly Lys Gly Ser Ile
115 120 125

Asp Thr Cys Ala Lys Phe Ser Cys Thr Ser Lys Ala Ile Gly Arg Thr
130 135 140

Ile Gln Ser Glu Asn Ile Lys Tyr Glu Val Gly Ile Phe Val His Gly
145 150 155 160

Thr Thr Thr Ser Glu Asn His Gly Asn Tyr Ser Ala Gln Val Gly Ala
165 170 175

Ser Gln Ala Ala Lys Phe Thr Val Thr Pro Asn Ala Pro Ser Ile Thr
180 185 190

Leu Lys Leu Gly Asp Tyr Gly Glu Val Thr Leu Asp Cys Glu Pro Arg
195 200 205

Ser Gly Leu Asn Thr Glu Ala Phe Tyr Val Met Thr Val Gly Ser Lys
210 215 220

Ser Phe Leu Val His Arg Glu Trp Phe His Asp Leu Ala Leu Pro Trp
225 230 235 240

Thr Pro Pro Ser Ser Thr Ala Trp Arg Asn Arg Glu Leu Leu Met Glu
245 250 255

Phe Glu Glu Ala His Ala Thr Lys Gln Ser Val Val Ala Leu Gly Ser
260 265 270

Gln Glu Gly Gly Leu His Gln Ala Leu Ala Gly Ala Ile Val Val Glu
275 280 285

-continued

```
Tyr Ser Ser Ser Val Lys Leu Thr Ser Gly His Leu Lys Cys Arg Leu
    290                 295                 300

Lys Met Asp Lys Leu Ala Leu Lys Gly Thr Thr
305                 310                 315


<210> SEQ ID NO 4
<211> LENGTH: 500
<212> TYPE: PRT
<213> ORGANISM: Japanese encephalitis virus

<400> SEQUENCE: 4

Phe Asn Cys Leu Gly Met Gly Asn Arg Asp Phe Ile Glu Gly Ala Ser
 1               5                  10                  15

Gly Ala Thr Trp Val Asp Leu Val Leu Glu Gly Asp Ser Cys Leu Thr
            20                  25                  30

Ile Met Ala Asn Asp Lys Pro Thr Leu Asp Val Arg Met Ile Asn Ile
        35                  40                  45

Glu Ala Ser Gln Leu Ala Glu Val Arg Ser Tyr Cys Tyr His Ala Ser
    50                  55                  60

Val Thr Asp Ile Ser Thr Val Ala Arg Cys Pro Thr Thr Gly Glu Ala
65                  70                  75                  80

His Asn Glu Lys Arg Ala Asp Ser Ser Tyr Val Cys Lys Gln Gly Phe
                85                  90                  95

Thr Asp Arg Gly Trp Gly Asn Gly Cys Gly Leu Phe Gly Lys Gly Ser
            100                 105                 110

Ile Asp Thr Cys Ala Lys Phe Ser Cys Thr Ser Lys Ala Ile Gly Arg
        115                 120                 125

Thr Ile Gln Ser Glu Asn Ile Lys Tyr Glu Val Gly Ile Phe Val His
    130                 135                 140

Gly Thr Thr Thr Ser Glu Asn His Gly Asn Tyr Ser Ala Gln Val Gly
145                 150                 155                 160

Ala Ser Gln Ala Ala Lys Phe Thr Val Thr Pro Asn Ala Pro Ser Ile
                165                 170                 175

Thr Leu Lys Leu Gly Asp Tyr Gly Glu Val Thr Leu Asp Cys Glu Pro
            180                 185                 190

Arg Ser Gly Leu Asn Thr Glu Ala Phe Tyr Val Met Thr Val Gly Ser
        195                 200                 205

Lys Ser Phe Leu Val His Arg Glu Trp Phe His Asp Leu Ala Leu Pro
    210                 215                 220

Trp Thr Pro Pro Ser Ser Thr Ala Trp Arg Asn Arg Glu Leu Leu Met
225                 230                 235                 240

Glu Phe Glu Glu Ala His Ala Thr Lys Gln Ser Val Val Ala Leu Gly
                245                 250                 255

Ser Gln Glu Gly Gly Leu His Gln Ala Leu Ala Gly Ala Ile Val Val
            260                 265                 270

Glu Tyr Ser Ser Ser Val Lys Leu Thr Ser Gly His Leu Lys Cys Arg
        275                 280                 285

Leu Lys Met Asp Lys Leu Ala Leu Lys Gly Thr Thr Tyr Gly Met Cys
    290                 295                 300

Thr Glu Lys Phe Ser Phe Ala Lys Asn Pro Ala Asp Thr Gly His Gly
305                 310                 315                 320

Thr Val Val Ile Glu Leu Ser Tyr Ser Gly Ser Asp Gly Pro Cys Lys
                325                 330                 335

Ile Pro Ile Val Ser Val Ala Ser Leu Asn Asp Met Thr Pro Val Gly
            340                 345                 350
```

-continued

```
Arg Leu Val Thr Val Asn Pro Phe Val Ala Thr Ser Ser Ala Asn Ser
        355                 360                 365

Lys Val Leu Val Glu Met Glu Pro Pro Phe Gly Asp Ser Tyr Ile Val
    370                 375                 380

Val Gly Arg Gly Asp Lys Gln Ile Asn His His Trp Tyr Lys Ala Gly
385                 390                 395                 400

Ser Thr Leu Gly Lys Ala Phe Ser Thr Thr Leu Lys Gly Ala Gln Arg
                405                 410                 415

Leu Ala Ala Leu Gly Asp Thr Ala Trp Asp Phe Gly Ser Ile Gly Gly
            420                 425                 430

Val Phe Asn Ser Ile Gly Lys Ala Val His Gln Val Phe Gly Gly Ala
        435                 440                 445

Phe Arg Thr Leu Phe Gly Gly Met Ser Trp Ile Thr Gln Gly Leu Met
    450                 455                 460

Gly Ala Leu Leu Leu Trp Met Gly Ile Asn Ala Arg Asp Arg Ser Ile
465                 470                 475                 480

Ala Leu Ala Phe Leu Ala Thr Gly Gly Val Leu Val Phe Leu Ala Thr
                485                 490                 495

Asn Val His Ala
            500


<210> SEQ ID NO 5
<211> LENGTH: 15
<212> TYPE: PRT
<213> ORGANISM: Japanese encephalitis virus

<400> SEQUENCE: 5

Val Val Phe Thr Ile Leu Leu Leu Leu Val Ala Pro Ala Tyr Ser
 1               5                  10                  15


<210> SEQ ID NO 6
<211> LENGTH: 900
<212> TYPE: DNA
<213> ORGANISM: Japanese encephalitis virus

<400> SEQUENCE: 6

ttcaactgtc tgggaatggg caatcgtgac ttcatagaag gagccagtgg agccacttgg      60

gtggacttgg tgctagaagg agacagctgc ttgacaatca tggcaaacga caaaccaaca     120

ttggacgtcc gcatgatcaa catcgaagct agccaacttg ctgaggtcag aagttactgc     180

tatcatgctt cagtcactga catctcgacg gtggctcggt gccccacgac tggagaagcc     240

cacaacgaga agcgagctga tagtagctat gtgtgcaaac aaggcttcac tgatcgtggg     300

tggggcaacg gatgtggact tttcgggaag ggaagtattg acacatgtgc aaaattctcc     360

tgcaccagca aagcgattgg aagaacaatc cagtcagaaa acatcaaata cgaagttggc     420

atttttgtgc atggaaccac cacttcggaa aaccatggga attattcagc gcaagttggg     480

gcgtcccagg cggcaaagtt tacagtaaca cctaatgctc cttcgataac cctcaaactt     540

ggtgactacg gagaagtcac actggactgt gagccaagga gtggactaaa cactgaagcg     600

ttttacgtca tgaccgtggg gtcaaagtca tttttggtcc atagggaatg gtttcatgac     660

ctcgctctcc cttggacgcc cccttcgagc acagcgtgga gaaacagaga actcctcatg     720

gaatttgaag aggcgcacgc cacaaaacag tccgttgttg ctcttgggtc acaggaagga     780

ggcctccatc aggcgttggc aggagccatc gtggtggagt actcaagctc agtgaagtta     840

acatcaggcc acctaaaatg caggctgaaa atggacaaac tggctctgaa aggcacaacc     900
```

-continued

<210> SEQ ID NO 7
<211> LENGTH: 480
<212> TYPE: DNA
<213> ORGANISM: Japanese encephalitis virus

<400> SEQUENCE: 7
gacaaactgg ctctgaaagg cacaacctat ggtatgtgca cagaaaaatt ctcgttcgcg 60
aaaaatccgg cggacactgg tcacggaaca gttgtcattg aactttcata ctctgggagt 120
gatggcccct gcaagattcc gattgtctcc gttgctagcc tcaatgacat gacccccgtc 180
gggcggctgg tgacggtgaa ccccttcgtc gcgacttcca gcgccaactc aaaggtgctg 240
gtcgagatgg aacccccctt cggagactcc tacatcgtag ttggaagggg agacaagcag 300
attaaccacc attggtacaa ggctggaagc acgctgggca aagccttttc aacgactttg 360
aagggagctc aaagactggc agcgttgggc gacacagcct gggactttgg ctctattgga 420
ggggtcttca actccatagg gaaagctgtt caccaagtgt ttggtggtgc cttcagaaca 480

<210> SEQ ID NO 8
<211> LENGTH: 945
<212> TYPE: DNA
<213> ORGANISM: Japanese encephalitis virus

<400> SEQUENCE: 8
gtggtattca ccatcctcct gctgttggtc gctccggctt atagtttcaa ctgtctggga 60
atgggcaatc gtgacttcat agaaggagcc agtggagcca cttgggtgga cttggtgcta 120
gaaggagaca gctgcttgac aatcatggca aacgacaaac caacattgga cgtccgcatg 180
atcaacatcg aagctagcca acttgctgag gtcagaagtt actgctatca tgcttcagtc 240
actgacatct cgacggtggc tcggtgcccc acgactggag aagcccacaa cgagaagcga 300
gctgatagta gctatgtgtg caaacaaggc ttcactgatc gtgggtgggg caacggatgt 360
ggacttttcg ggaagggaag tattgacaca tgtgcaaaat tctcctgcac cagcaaagcg 420
attggaagaa caatccagtc agaaaacatc aaatacgaag ttggcatttt tgtgcatgga 480
accaccactt cggaaaacca tgggaattat tcagcgcaag ttggggcgtc ccaggcggca 540
aagtttacag taacacctaa tgctccttcg ataaccctca aacttggtga ctacggagaa 600
gtcacactgg actgtgagcc aaggagtgga ctaaacactg aagcgtttta cgtcatgacc 660
gtggggtcaa agtcattttt ggtccatagg gaatggtttc atgacctcgc tctcccttgg 720 acgcccccctt cgagcacagc gtggagaaac agagaactcc tcatggaatt tgaagaggcg 780
cacgccacaa aacagtccgt tgttgctctt gggtcacagg aaggaggcct ccatcaggcg 840
ttggcaggag ccatcgtggt ggagtactca agctcagtga agttaacatc aggccaccta 900
aaatgcaggc tgaaaatgga caaactggct ctgaaaggca caacc 945

<210> SEQ ID NO 9
<211> LENGTH: 1500
<212> TYPE: DNA
<213> ORGANISM: Japanese encephalitis virus

<400> SEQUENCE: 9
ttcaactgtc tgggaatggg caatcgtgac ttcatagaag gagccagtgg agccacttgg 60
gtggacttgg tgctagaagg agacagctgc ttgacaatca tggcaaacga caaaccaaca 120
ttggacgtcc gcatgatcaa catcgaagct agccaacttg ctgaggtcag aagttactgc 180
tatcatgctt cagtcactga catctcgacg gtggctcggt gccccacgac tggagaagcc 240

-continued

```
cacaacgaga agcgagctga tagtagctat gtgtgcaaac aaggcttcac tgatcgtggg    300

tggggcaacg gatgtggact tttcgggaag ggaagtattg acacatgtgc aaaattctcc    360

tgcaccagca aagcgattgg aagaacaatc cagtcagaaa acatcaaata cgaagttggc    420

atttttgtgc atggaaccac cacttcggaa aaccatggga attattcagc gcaagttggg    480

gcgtcccagg cggcaaagtt tacagtaaca cctaatgctc cttcgataac cctcaaactt    540

ggtgactacg gagaagtcac actggactgt gagccaagga gtggactaaa cactgaagcg    600

ttttacgtca tgaccgtggg gtcaaagtca tttttggtcc atagggaatg gtttcatgac    660

ctcgctctcc cttggacgcc cccttcgagc acagcgtgga gaaacagaga actcctcatg    720

gaatttgaag aggcgcacgc cacaaaacag tccgttgttg ctcttgggtc acaggaagga    780

ggcctccatc aggcgttggc aggagccatc gtggtggagt actcaagctc agtgaagtta    840

acatcaggcc acctaaaatg caggctgaaa atggacaaac tggctctgaa aggcacaacc    900

tatggtatgt gcacagaaaa attctcgttc gcgaaaaatc cggcggacac tggtcacgga    960

acagttgtca ttgaactttc atactctggg agtgatggcc cctgcaagat tccgattgtc   1020

tccgttgcta gcctcaatga catgaccccc gtcgggcggc tggtgacggt gaacccctc    1080

gtcgcgactt ccagcgccaa ctcaaaggtg ctggtcgaga tggaaccccc cttcggagac   1140

tcctacatcg tagttggaag gggagacaag cagattaacc accattggta caaggctgga   1200

agcacgctgg gcaaagcctt ttcaacgact ttgaagggag ctcaaagact ggcagcgttg   1260

ggcgacacag cctgggactt tggctctatt ggaggggtct tcaactccat agggaaagct   1320

gttcaccaag tgtttggtgg tgccttcaga acactctttg gggaatgtc ttggatcaca    1380

caagggctaa tgggggccct actactttgg atgggcatca acgcacgaga ccgatcaatt   1440

gctttggcct tcttagccac aggaggtgtg ctcgtgttct tagctaccaa tgtgcatgct   1500
```

<210> SEQ ID NO 10
<211> LENGTH: 45
<212> TYPE: DNA
<213> ORGANISM: Japanese encephalitis virus

<400> SEQUENCE: 10

```
gtggtattca ccatcctcct gctgttggtc gctccggctt atagt                     45
```

<210> SEQ ID NO 11
<211> LENGTH: 174
<212> TYPE: PRT
<213> ORGANISM: Artificial Sequence
<220> FEATURE:
<223> OTHER INFORMATION: Synthetically generated peptide

<400> SEQUENCE: 11

```
Val Phe Thr Ile Leu Leu Leu Leu Val Ala Pro Ala Tyr Ser Asp Lys
 1               5                  10                  15

Leu Ala Leu Lys Gly Thr Thr Tyr Gly Met Cys Thr Glu Lys Phe Ser
            20                  25                  30

Phe Ala Lys Asn Pro Ala Asp Thr Gly His Gly Thr Val Val Ile Glu
        35                  40                  45

Leu Ser Tyr Ser Gly Ser Asp Gly Pro Cys Lys Ile Pro Ile Val Ser
    50                  55                  60

Val Ala Ser Leu Asn Asp Met Thr Pro Val Gly Arg Leu Val Thr Val
65                  70                  75                  80

Asn Pro Phe Val Ala Thr Ser Ser Ala Asn Ser Lys Val Leu Val Glu
                85                  90                  95
```

-continued

```
Met Glu Pro Pro Phe Gly Asp Ser Tyr Ile Val Val Gly Arg Gly Asp
            100                 105                 110

Lys Gln Ile Asn His His Trp Tyr Lys Ala Gly Ser Thr Leu Gly Lys
        115                 120                 125

Ala Phe Ser Thr Thr Leu Lys Gly Ala Gln Arg Leu Ala Ala Leu Gly
    130                 135                 140

Asp Thr Ala Trp Asp Phe Gly Ser Ile Gly Gly Val Phe Asn Ser Ile
145                 150                 155                 160

Gly Lys Ala Val His Gln Val Phe Gly Gly Ala Phe Arg Thr
                165                 170
```

<210> SEQ ID NO 12
<211> LENGTH: 525
<212> TYPE: DNA
<213> ORGANISM: Artificial Sequence
<220> FEATURE:
<223> OTHER INFORMATION: Synthetically generated oligonucleotide

<400> SEQUENCE: 12

```
gtggtattca ccatcctcct gctgttggtc gctccggctt atagtgacaa actggctctg     60

aaaggcacaa cctatggtat gtgcacagaa aaattctcgt tcgcgaaaaa tccggcggac    120

actggtcacg gaacagttgt cattgaactt tcatactctg ggagtgatgg cccctgcaag    180

attccgattg tctccgttgc tagcctcaat gacatgaccc ccgtcgggcg gctggtgacg    240

gtgaacccct tcgtcgcgac ttccagcgcc aactcaaagg tgctggtcga gatggaaccc    300

cccttcggag actcctacat cgtagttgga aggggagaca agcagattaa ccaccattgg    360

tacaaggctg gaagcacgct gggcaaagcc ttttcaacga ctttgaaggg agctcaaaga    420

ctggcagcgt tgggcgacac agcctgggac tttggctcta ttggaggggt cttcaactcc    480

atagggaaag ctgttcacca agtgtttggt ggtgccttca gaaca                    525
```

<210> SEQ ID NO 13
<211> LENGTH: 29
<212> TYPE: DNA
<213> ORGANISM: Artificial Sequence
<220> FEATURE:
<223> OTHER INFORMATION: Primer

<400> SEQUENCE: 13

```
cgcggatcca aatggtggta ttcaccatc                                       29
```

<210> SEQ ID NO 14
<211> LENGTH: 29
<212> TYPE: DNA
<213> ORGANISM: Artificial Sequence
<220> FEATURE:
<223> OTHER INFORMATION: Primer

<400> SEQUENCE: 14

```
ttttctagag cttaggttgt gcctttcag                                       29
```

<210> SEQ ID NO 15
<211> LENGTH: 29
<212> TYPE: DNA
<213> ORGANISM: Artificial Sequence
<220> FEATURE:
<223> OTHER INFORMATION: Primer

<400> SEQUENCE: 15

```
cgcggatcca aatgttcaac tgtctggga                                       29
```

-continued

<210> SEQ ID NO 16
<211> LENGTH: 29
<212> TYPE: DNA
<213> ORGANISM: Artificial Sequence
<220> FEATURE:
<223> OTHER INFORMATION: Primer

<400> SEQUENCE: 16
ttttctagag cttaggttgt gcctttcag 29

<210> SEQ ID NO 17
<211> LENGTH: 29
<212> TYPE: DNA
<213> ORGANISM: Artificial Sequence
<220> FEATURE:
<223> OTHER INFORMATION: Primer

<400> SEQUENCE: 17
cgcggatcca aatggtggta ttcaccatc 29

<210> SEQ ID NO 18
<211> LENGTH: 29
<212> TYPE: DNA
<213> ORGANISM: Artificial Sequence
<220> FEATURE:
<223> OTHER INFORMATION: Primer

<400> SEQUENCE: 18
ttttctagac gttatgttct gaaggcacc 29

<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19
gctgcatatg gacaaactgg ctctg 25

<210> SEQ ID NO 20
<211> LENGTH: 29
<212> TYPE: DNA
<213> ORGANISM: Artificial Sequence
<220> FEATURE:
<223> OTHER INFORMATION: Primer

<400> SEQUENCE: 20
ttttctagac gttatgttct gaaggcacc 29

<210> SEQ ID NO 21
<211> LENGTH: 1545
<212> TYPE: DNA
<213> ORGANISM: Japanese encephalitis virus

<400> SEQUENCE: 21
gtggtattca ccatcctcct gctgttggtc gctccggctt atagtttcaa ctgtctggga 60
atgggcaatc gtgacttcat agaaggagcc agtggagcca cttgggtgga cttggtgcta 120
gaaggagaca gctgcttgac aatcatggca aacgacaaac caacattgga cgtccgcatg 180
atcaacatcg aagctagcca acttgctgag gtcagaagtt actgctatca tgcttcagtc 240
actgacatct cgacggtggc tcggtgcccc acgactggag aagcccacaa cgagaagcga 300
gctgatagta gctatgtgtg caaacaaggc ttcactgatc gtgggtgggg caacggatgt 360

-continued

| | | | | | | |
|---|---|---|---|---|---|---|
| ggacttttcg | ggaagggaag | tattgacaca | tgtgcaaaat | tctcctgcac | cagcaaagcg | 420 |
| attggaagaa | caatccagtc | agaaaacatc | aaatacgaag | ttggcatttt | tgtgcatgga | 480 |
| accaccactt | cggaaaacca | tgggaattat | tcagcgcaag | ttggggcgtc | ccaggcggca | 540 |
| aagtttacag | taacacctaa | tgctccttcg | ataaccctca | aacttggtga | ctacggagaa | 600 |
| gtcacactgg | actgtgagcc | aaggagtgga | ctaaacactg | aagcgtttta | cgtcatgacc | 660 |
| gtggggtcaa | agtcattttt | ggtccatagg | gaatggtttc | atgacctcgc | tctcccttgg | 720 |
| acgccccctt | cgagcacagc | gtggagaaac | agagaactcc | tcatggaatt | tgaagaggcg | 780 |
| cacgccacaa | aacagtccgt | tgttgctctt | gggtcacagg | aaggaggcct | ccatcaggcg | 840 |
| ttggcaggag | ccatcgtggt | ggagtactca | agctcagtga | agttaacatc | aggccaccta | 900 |
| aaatgcaggc | tgaaaatgga | caaactggct | ctgaaaggca | caacctatgg | tatgtgcaca | 960 |
| gaaaaattct | cgttcgcgaa | aaatccggcg | gacactggtc | acggaacagt | tgtcattgaa | 1020 |
| ctttcatact | ctgggagtga | tggcccctgc | aagattccga | ttgtctccgt | tgctagcctc | 1080 |
| aatgacatga | cccccgtcgg | gcggctggtg | acggtgaacc | ccttcgtcgc | gacttccagc | 1140 |
| gccaactcaa | aggtgctggt | cgagatggaa | ccccccttcg | gagactccta | catcgtagtt | 1200 |
| ggaaggggag | acaagcagat | taaccaccat | tggtacaagg | ctggaagcac | gctgggcaaa | 1260 |
| gccttttcaa | cgactttgaa | gggagctcaa | agactggcag | cgttgggcga | cacagcctgg | 1320 |
| gactttggct | ctattggagg | ggtcttcaac | tccataggga | aagctgttca | ccaagtgttt | 1380 |
| ggtggtgcct | tcagaacact | ctttggggga | atgtcttgga | tcacacaagg | gctaatgggg | 1440 |
| gccctactac | tttggatggg | catcaacgca | cgagaccgat | caattgcttt | ggccttctta | 1500 |
| gccacaggag | gtgtgctcgt | gttcttagct | accaatgtgc | atgct | | 1545 |